United States Patent [19]

Lewis

[11] Patent Number: 4,500,294

[45] Date of Patent: Feb. 19, 1985

[54] METHOD AND DEVICE FOR DETECTING DENTAL CAVITIES

[75] Inventor: William D. Lewis, Flintridge, Calif.

[73] Assignee: Epic International Corporation, North Hollywood, Calif.

[21] Appl. No.: 538,568

[22] Filed: Oct. 3, 1983

[51] Int. Cl.³ .............................................. A61C 5/00
[52] U.S. Cl. .................................................. 433/215
[58] Field of Search ......................... 433/32, 27, 215; 128/736, 742

[56] References Cited

U.S. PATENT DOCUMENTS 4,064,872 12/1977 Caplan ................................. 128/736
4,324,547 4/1980 Arcan .................................... 433/71
4,378,808 4/1983 Lichtenstein ........................ 128/736

Primary Examiner—Robert Peshock
Attorney, Agent, or Firm—Freilich, Hornbaker, Rosen & Fernandez

[57] ABSTRACT

A method and device for detecting tooth decay by utilizing a temperature sensitive material brought into contact with a user's teeth to visibly indicate a temperature differential between teeth in close proximity to each other.

16 Claims, 5 Drawing Figures

U.S. Patent   Feb. 19, 1985   4,500,294
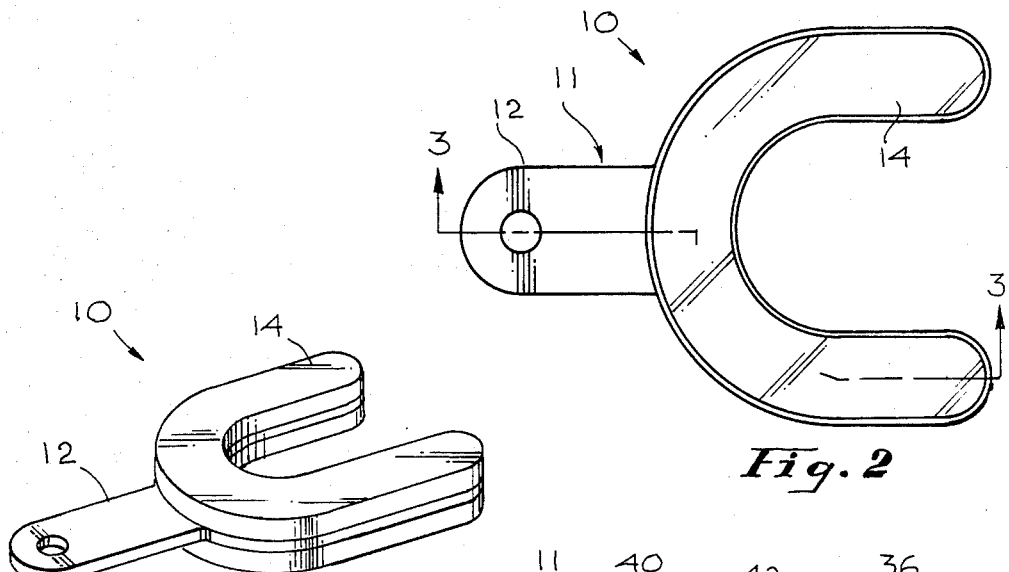
Fig. 1
Fig. 2
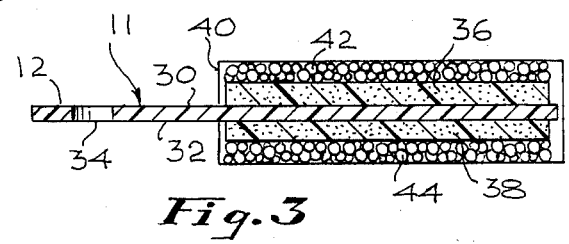
Fig. 3
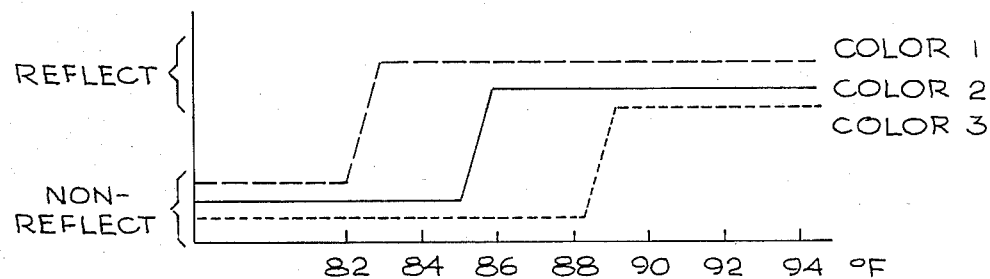
Fig. 4
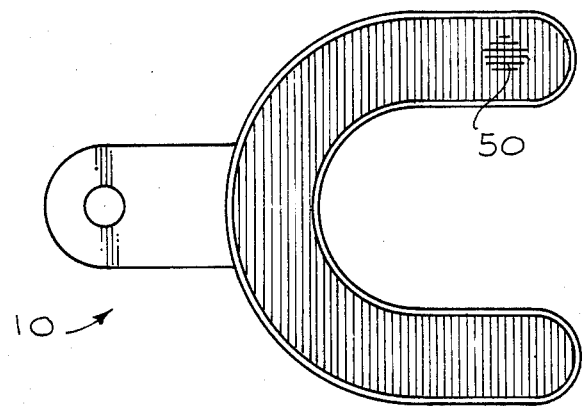
Fig. 5

METHOD AND DEVICE FOR DETECTING DENTAL CAVITIES

BACKGROUND OF THE INVENTION

This invention relates generally to a method and devices for detecting dental cavities and more particularly to a device intended for placement between a user's upper and lower teeth to quickly detect elevated temperatures associated with tooth decay.

It has been reported in the dental literature that a decaying tooth constitutes a "hot spot" in the mouth, having a surface temperature slightly higher than that of adjacent healthy teeth. Accordingly, it has been suggested that an infrared camera could be designed for use by dentists to supplement their traditional methods of detecting tooth decay.

SUMMARY OF THE INVENTION

The present invention is directed to a device which can be inexpensively produced and used by an individual to check his own mouth for tooth decay. The device is primarily intended for mass distribution, preferably as a disposable item, to enable a user to conveniently and regularly check his own teeth to alert him when to visit a dentist. The teachings of the invention are also applicable for use by dentists to supplement their traditional methods of examination.

In more particularity, the present invention is directed to a device including a substantially flat support member intended to be temporarily placed between a user's upper and lower teeth. The support member carries a material thereon whose visible characteristics vary as a function of temperature. By biting down on the support member, a user will bring his teeth into contact with the temperature sensitive material. As a consequence, the temperature differential between the user's healthy teeth and a decayed tooth will produce a visible change on the material which can be readily recognized by the user upon removal of the device.

In a preferred embodiment, the support member includes a handle portion and a detector portion. The detector portion, which is U-shaped to easily fit within a user's mouth between his upper and lower teeth, carries temperature sensitive material on its upper and lower surfaces.

In accordance with the preferred embodiment, the temperature sensitive material comprises liquid crystal based compositions encapsulated in transparent microcapsules.

The temperature sensitive properties of liquid crystals are well known and are used, for example, in commercially available fever thermometers; e.g., FeverScan thermometers marketed by American Thermometer Company. See also U.S. Pat. Nos. 3,175,401 and 4,150,572. In these devices, multiple compartments are typically provided with each containing a different liquid crystal based composition. Such compositions are selected for their ability to undergo a visible change at a different predetermined temperature. Thus, for example, when the temperature of such a composition crosses a certain threshold, its appearance will change from dark to light, or vice versa. It is also known that liquid crystal based compositions can produce different color effects (for example, see *Chemical and Engineering Magazine,* Jan. 31, 1983, page 24, "Liquid Crystals, a Colorful State of Matter"). That is, each different liquid crystal based composition can reflect a different color as its temperature is increased.

In accordance with the preferred embodiment of the present invention, multiple liquid crystal compositions are utilized, each capable of producing a different reflected color at a different temperature threshold. Each different composition is distributed amongst a great many microcapsules, i.e., a microcapsule color group. The microcapsules from the multiple color groups are distributed substantially uniformly on the surface of the detector portion of the support member. Thus, when the surface is exposed to a substantially uniform temperature, e.g., healthy teeth, the light reflected from the surface will be of substantially uniform color. However, when exposed to a plurality of teeth which includes a decaying tooth, the decaying tooth will produce a unique change on the temperature sensitive material which can then be readily visually recognized by the user.

DESCRIPTION OF THE DRAWINGS

FIG. 1 is an isometric view of a preferred embodiment of the present invention;

FIG. 2 is a plan view of the device depicted in FIG. 1;

FIG. 3 is a sectional view taken substantially along the plane 3—3 of FIG. 2;

FIG. 4 comprises a graphical representation of the characteristics of multiple liquid crystal based compositions utilized in the device illustrated in FIGS. 1-3; and FIG. 5 is a schematic representation showing the color effects typically produced by use of a device in accordance with the invention.

DESCRIPTION OF THE PREFERRED EMBODIMENT

Attention is now directed to FIG. 1 which illustrates a preferred embodiment of a device in accordance with the present invention for detecting dental cavities. The device 10 is basically comprised of a handle portion 12 and a detector portion 14. The detector portion 14 is essentially U-shaped and dimensioned so as to approximate the jawline of a user. Both the handle portion 12 and detector portion 14 are essentially flat and define upper and lower surfaces. As will be discussed in greater detail hereinafter, the upper and lower surfaces of the detector portion 14 have temperature sensitive material affixed thereto. The device 10 is intended to be utilized by a person who grasps the handle 12 and inserts the detector portion 14 into his mouth so that the arms of the U-shaped portion 14 extend between his upper and lower teeth. The user can then bite down to bring his upper and lower teeth concurrently into contact with the temperature sensitive material carried by the upper and lower surfaces of the detector portion.

Prior to proceeding to a more detailed explanation of the construction and utilization of the device depicted in FIG. 1, it should be noted that the device 10 is intended for mass distribution, preferably as a disposable item, to allow users to periodically check their own teeth for signs of tooth decay. The device 10 is not intended as a substitute for regular dental check ups, but rather as a means by which a user can examine his teeth between such check ups to determine whether an extra visit to the dentist might be advisable. Additionally, the device depicted in FIG. 1, can be used by dentists in order to supplement their examination of a patient's teeth.

The method and device for detecting tooth decay in accordance with the present invention is based upon the recognition that a decaying tooth typically exhibits a surface temperature which is higher than healthy teeth in the same mouth. The temperature difference, $\Delta T$ is dependent upon the degree of decay but is typically between 1 and 5 degrees Fahrenheit. That is, in a typical mouth where the surface temperature of the healthy teeth is 80° F., a decaying tooth would typically exhibit a surface temperature 2° or 3° higher.

In accordance with the invention, in order to detect this temperature differential between a decaying tooth and healthy teeth, a temperature sensitive material is brought into contact with the teeth. The material is then examined for visible changes produced thereon as a consequence of the temperature differential.

In the preferred embodiment of the invention, multiple liquid crystal based compositions are utilized to form the temperature sensitive material which is then affixed to the upper and lower surfaces of the aforementioned detector portion 14. The utilization of liquid crystal based compositions for temperature detection is readily known and widely discussed in the literature. That is, it is known that different liquid crystal based compositions are available which can change their optical properties as their temperature varies. Most simply, the change in optical properties comprises switching from being reflective to non-reflective, or vice versa. Liquid crystal based compositions are also known which can produce color effects such that when a threshold temperature is exceeded, the composition will reflect light of a particular color.

In accordance with the present invention, liquid crystal based compositions are utilized which are operative over the temperature range of about 76° F. to 86° F. to reflect different colors as a function of temperature. In the preferred embodiment multiple compositions are utilized, each having a different threshold temperature, and each reflecting a different color as its threshold temperature is exceeded. FIG. 4 depicts the basic characteristics of three different liquid crystal based compositions utilized in accordance with the preferred embodiment. Thus, the dashed line plot 20 exhibits the characteristic of a first liquid crystal based composition which is depicted as being nonreflective below a first temperature threshold (T1) of 82° F. Above 82° F., it will reflect, or appear to flow with light of a first color (color 1).

Plot 22 depicted in solid line in FIG. 4 represents a second liquid crystal based composition which gives off light of a second color (color 2) as its temperature exceeds a second temperature threshold (T2) of 85° F. Plot 24, depicted in dotted line in FIG. 4, represents a liquid crystal based composition which gives off light of a third color (color 3) as its temperature exceeds a third temperature threshold (T3) of 88° F.

Liquid crystal based compositions which function as generally represented in FIG. 4 are known in the literature. For the applications contemplated for the present invention, the compositions should be selected so as to cover the temperature spectrum typically encountered with a variety of users, i.e., on the order of 76° F. to 86° F., for healthy teeth. Decaying teeth for the same users would exhibit a temperature spectrum typically 2° to 3° higher.

Within these temperature spectrums, multiple temperature sensitive compositions are preferably selected. FIG. 4 illustrates the characteristics of three different liquid crystal based compositions but indeed, it should be understood, that embodiments of the invention could use either a smaller or larger number of compositions such as four or five. Regardless of the number of different compositions utilized, it is important that they collectively exhibit different temperature thresholds within the expected temperature spectrum and respond by reflecting light of different colors.

In accordance with applicant's preferred embodiment, the multiple liquid crystal based compositions are packaged in transparent microcapsules typically less than 400 microns in diameter. Packaging in microcapsules is well known in the art and is commercially available from different companies, e.g., EURAND America, Inc. or Minnesota Mining and Manufacturing Company. Accordingly, in accordance with the preferred embodiment, each liquid crystal based composition is packaged in a great many transparent microcapsules, defining a microcapsule color group. Where three different liquid crystal based compositions are utilized, as is represented by FIG. 4, three different microcapsule color groups are utilized. As is well known, the microcapsules can be carried in a slurry which can be applied to a surface as by brushing or spraying.

Attention is now directed to FIGS. 2 and 3 which illustrate the device 10 in greater detail. The device 10 is comprised of a support member 11, preferably formed of semi rigid plastic material, shaped to define the aforementioned U-shaped detector portion 14 and handle portion 12 extending from the bight area of the U-shape. The support member 11 is essentially flat defining an upper surface 30 and a lower surface 32. A hole 34 is formed in the handle 12 to allow the device to be readily hung on a hook when on display or otherwise not in use.

First and second layers 36, 38 of a medium soft material, e.g., polyurethane, are adhered to the upper and lower surfaces 30 and 32 of the U-shaped detector portion 14. The temperature sensitive material, i.e., the aforementioned microcapsules, are then affixed to the outer surfaces of the layers 36, 38.

More particularly, the multiple microcapsule color groups are mixed, preferably in a slurry, so as to essentially be uniformly distributed. The uniform mixture is then applied to the outer surfaces of the layers 36, 38 as by brushing or spraying. A solid translucent flexible covering 40 can then be applied to protect the microcapsules layers 42, 44.

In the use of the device 10, a user will grasp the handle portion 12 and place the detector portion 14 in his mouth between his upper and lower teeth. He will then bite down upon the detector portion, bringing his upper and lower teeth into contact with the upper and lower layers 42, 44 of microcapsules. It should be recognized that the capsules are sufficiently small, i.e., less than 400 microns, so that a great many will be brought into contact with each tooth. On the assumption that most of the teeth in the mouth are healthy, they will all have the same effect on the temperature sensitive material that they come in contact with. Depending upon the surface temperature of the user's healthy teeth, a visible change may or may not be produced in the temperature sensitive material layers. However, the presence of a decaying tooth will produce a special visual indication, e.g., it may provide the only area exhibiting color 3. Accordingly, when the user removes the device 10 from his mouth and examines it, he will be able to determine the existence of a decaying tooth and the location of that tooth. FIG. 5 schematically depicts how the upper layer of the detector portion might appear after use, showing a small area 50 of blue on an otherwise reddish background.

From the foregoing, it should now be appreciated that a device and method for detecting tooth decay has been disclosed herein. Although a specific preferred embodiment has been disclosed, it is recognized that variations and modifications will readily occur to those skilled in the art and it is intended that the claims hereof cover such. For example only, it is recognized that the device 10 need not be shaped as illustrated, but can indeed merely comprise a strip which may then require that the user examine the sides of his mouth separately. Further, it is not essential that the temperature sensitive material be applied to both upper and lower surfaces of the device. The material could be available on one side only, thereby requiring that the upper and lower teeth be examined separately. Still further, although a preferred form of temperature sensitive material, i.e., multiple liquid crystal based compositions, has been disclosed herein, it is recognized that other compositions or materials may be appropriate.

I claim:

1. A device for detecting tooth decay comprising:
a support member having upper and lower surfaces adapted for placement in a user's mouth for concurrent engagement of said upper surface against the user's upper teeth and said lower surface against the user's lower teeth;
temperature sensing means responsive to a temperature in excess of a first threshold temperature T1 for producing a first visible indication and responsive to a temperature in excess of a second threshold temperature T2 for producing a second visible indication, distinguishable from said first visible indication; and
means affixing said temperature sensing means to said support member upper surface for contacting multiple ones of said user's upper teeth, said temperature sensing means exhibiting a substantially uniform response across said upper surface whereby teeth of the same temperature will cause said sensing means to produce the same visible indications.

2. The device of claim 1 wherein said support member is substantially U-shaped to conform to a user's jaw line; and wherein
each of said upper and lower surfaces has said temperature sensing means affixed thereto.

3. The device of claim 2 including a handle member projecting outwardly from the bight portion of said U-shaped support member.

4. The device of claim 1 wherein said temperature sensing means is comprised of a liquid crystal based composition.

5. The device of claim 1 wherein said means affixing said temperature sensing means includes a plurality of transparent microcapsules containing said temperature sensing means.

6. The device of claim 5 wherein said temperature sensing means comprises different first and second liquid crystal based compositions respectively contained in first and second groups of microcapsules, said first and second groups being substantially uniformly distributed on said upper surface.

7. The device of claim 6 wherein said first liquid crystal based composition reflects light of a first color when its temperature exceeds T1 and wherein said second liquid crystal based composition reflects light of a second color when its temperature exceeds T2.

8. The device of claim 7 wherein said support member comprises a substantially flat strip defining said upper and lower surfaces thereon; and wherein
said means affixing said temperature sensing means further includes first and second layers of material respectively secured to said upper and lower surfaces; and wherein
a first plurality of said first microcapsule group and a first plurality of said second microcapsule group are interspersed and substantially uniformly distributed on said first layer; and wherein
a second plurality of said first microcapsule group and a second plurality of said second microcapsule group are interspersed and substantially uniformly distributed on said second layer.

9. A method of examining a group of teeth to detect a decayed tooth within the group, comprising the steps of:
bringing a strip of substantially uniform temperature sensitive material into contact with said group of teeth; and thereafter
visually examining said strip to locate color variations thereon.

10. The method of claim 9 wherein said step of bringing said strip into contact with said teeth includes concurrently contacting substantially all of a user's upper and lower teeth.

11. A device for detecting tooth decay comprising:
an essentially flat U-shaped support member having substantially parallel upper and lower surfaces, said member being shaped to be received in a user's mouth whereby said user can bite down on said support member to engage said upper surface against multiple ones of said user's upper teeth and said lower surface against multiple ones of said user's lower teeth; and
temperature sensing means affixed to said support member upper surface adapted to contact said user's upper teeth for producing a first visible indication in response to a temperature in excess of a first threshold temperature T1 and a second visible indication, distinguishable from said first visible indication, in response to a temperature in excess of a second threshold temperature T2, said temperature sensing means exhibiting a uniform response over the entire area of said upper surface whereby healthy teeth having a temperature between T1 and T2 will produce said first visible indication and decaying teeth having a temperature in excess of T2 will produce said second visible indication.

12. The device of claim 11 including a plurality of tightly packed transparent microcapsules affixed to said support member upper surface; and wherein
said temperature sensing means comprises first and second different liquid crystal based compositions contained in said microcapsules substantially uniformly distributed across said upper surface.

13. The device of claim 12 wherein said first liquid crystal based composition reflects light of a first color when its temperature exceeds said first threshold temperature T1 and wherein said second liquid crystal based composition reflects light of a second color when its temperature exceeds said second threshold temperature T2.

14. The device of claim 13 wherein said microcapsules are less than 400 microns in size whereby a large number of microcapsules will be contacted by each of said contacting teeth.

15. The device of claim 11 wherein said support member is formed in part by a layer of medium soft material defining said upper surface whereby said material and said temperature sensing means affixed to the upper surface thereof will make good confirming contact with the user's teeth when said user bites down on said support member.

16. The device of claim 11 wherein said temperature sensing means is also affixed to said lower surface whereby said user can bite down on said support member to concurrently engage said multiple ones of said upper teeth and said lower teeth against said temperature sensing means; and wherein said support member includes a compliant layer to which said temperature sensing means is affixed for allowing said temperature sensing means to make good conforming contact with said user's teeth.

* * * * *